US 9,480,393 B2

(12) United States Patent
Boate et al.

(10) Patent No.: US 9,480,393 B2
(45) Date of Patent: Nov. 1, 2016

(54) SYSTEM AND METHOD FOR ASSESSING RETINAL FUNCTIONALITY

(75) Inventors: Alan Boate, Ottawa (CA); Jeremy Lloyd Gribben, Ottawa (CA)

(73) Assignee: ANNIDIS CORPORATION (CA)

( * ) Notice: Subject to any disclaimer, the term of this patent is extended or adjusted under 35 U.S.C. 154(b) by 116 days.

(21) Appl. No.: 14/345,164

(22) PCT Filed: Sep. 14, 2012

(86) PCT No.: PCT/CA2012/000852
§ 371 (c)(1),
(2), (4) Date: Mar. 14, 2014

(87) PCT Pub. No.: WO2013/037050
PCT Pub. Date: Mar. 21, 2013

(65) Prior Publication Data
US 2014/0333898 A1    Nov. 13, 2014

Related U.S. Application Data

(60) Provisional application No. 61/535,693, filed on Sep. 16, 2011.

(51) Int. Cl.
*A61B 3/10* (2006.01)
*A61B 3/00* (2006.01)
*A61B 3/12* (2006.01)
*A61B 5/0484* (2006.01)

(52) U.S. Cl.
CPC ........... *A61B 3/0041* (2013.01); *A61B 3/0008* (2013.01); *A61B 3/12* (2013.01); *A61B 5/04842* (2013.01); *A61B 2576/02* (2013.01)

(58) Field of Classification Search
USPC .................................................. 351/221, 246
See application file for complete search history.

(56) References Cited

U.S. PATENT DOCUMENTS 5,052,401 A    10/1991  Sherwin
2004/0024287 A1    2/2004  Patton et al.

FOREIGN PATENT DOCUMENTS

WO    01/85045 A1    11/2001
WO    2011106783 A3   9/2011

OTHER PUBLICATIONS

International Search Report issued in corresponding International Patent Application No. PCT/CA2012/000852 on Feb. 18, 2013. (4 pp.).
Extended European Search Report mailed in corresponding European Patent Application No. 12831086.9 on Mar. 4, 2015. (6 pp.).

*Primary Examiner* — Jack Dinh
(74) *Attorney, Agent, or Firm* — Volpe and Koenig, P.C.

(57) ABSTRACT

A system and method for assessing the functionality of a visual system of the eye using a digital micro-mirror device (DMD) to generate a coded pattern which is illuminated by a light source. Optics project an image of the coded pattern onto the retina of the eye. Sensors detect electrical signals based on the response of the visual system to the image. One or more processors control the DMD and correlate the electrical response from the sensor with the coded DMD pattern to assess the functionality of the visual system.

20 Claims, 8 Drawing Sheets

SYSTEM AND METHOD FOR ASSESSING RETINAL FUNCTIONALITY

CROSS-REFERENCE TO RELATED APPLICATIONS

This application is related to and claims priority from U.S. Provisional patent application No. 61/535,693 filed 16 Sep. 2011, the entire contents of which are incorporated herein by reference.

TECHNICAL FIELD

This invention relates to systems and methods for assessing functionality of the retina and associated parts of the visual system using an optical stimulator device, and finds application in the fields of medicine and clinical research, especially electrophysiology and psychophysics. The invention also relates to optical stimulators for use in such systems and methods.

BACKGROUND

Optical stimulators are widely used to generate patterns of light for illumination of the retina of a subject. For convenience, in this specification, the term "optical stimulator" will be used to embrace stimulators emitting either visible or non-visible light, or both. The subject's response to the stimulus may be conscious or not. For example, the responses can be:
  (i) from the neural retinal, as in the ERG (Electroretinogram) and its variants, PERG (Pattern ERG), focal ERG or mfERG (multifocal ERG), detected by one or more electrodes on or near the anterior surface of the eye,
  (ii) from the optic nerve, as in the VEP (Visually Evoked Potential), detected by one or more electrodes at the back of the skull,
  (iii) from the visual cortex or other brain areas as detected by electrodes in various locations on the skull as in an EEG (electroencephalogram)
as perceived and reported by the subject, as in (micro) perimetry, or a large variety of psychophysics experiments or diagnostics which attempt to measure responses from various processing locations and levels in the visual system.

For convenience, the term electroretinogram will be used herein to embrace systems in which any of responses (i), (ii), (iii) and (iv) are evoked by optical stimulation of the eye, specifically the retina, and detected using attached electrodes. However, some responses (iv) might be detected by other means, for example by the subject activating a push-button switch.

These responses are evoked using an optical stimulator to apply optical stimuli to the eye. It is known to use halogen lamps or other discrete light sources for simple stimuli, while cathode ray tubes (CRTs) have been preferred for generating more complex optical stimuli. Although CRTs have seen widespread use in optical stimulators, they are not entirely satisfactory for a variety of reasons. For example, the patterns are "painted" pixel by pixel, horizontal line by horizontal line, with a fixed frame rate, typically 60 or 75 frames per second. They generate an impulse of light from each pixel as the electron beam excites the phosphor and which lasts for a few milliseconds. The spectral content of the stimuli is determined by the phosphors used and, apart from limited adjustment of the red, green, blue [RGB] mix, cannot be altered or controlled by the user. In general, frame rates are those useful for displaying video (typically 100 Hz or less) and are fixed, i.e. all frames will have the same duration. Typical luminance levels for CRTs are between 100 and 400 candelas/sq. meter which might be adequate for some stimuli but perhaps too low for others. Moreover, the luminance levels decrease as the CRT ages. Finally, the commercial availability of CRTs has been declining and clinicians, experimenters and instrument makers have been actively seeking suitable alternatives.

Alternatives include liquid crystal display (LCD) and light emitting diode (LED) screens and arrays of large numbers of discrete LEDS. However, these alternatives also are not entirely suitable for use in optical stimulators. Like CRTs, they usually have a fixed frame rate but now the stimulus is on for most of the frame period, going from 1 to 2 milliseconds with a CRT to 13 milliseconds or 16 milliseconds (75 Hz and 60 Hz frame rates) with a LCD. This longer duration changes the assumptions on which many of the electrophysiology measurements are made, i.e. that the stimulus is an impulse. The pixel update proceeds by horizontal rows, with a change period of a few milliseconds as the liquid crystals rotate to a new position. During this time a moving band of light leakage from the backlight has been noted in many displays, which can degrade the optical stimulus spatial/temporal format. Attempts to ameliorate this problem included building custom controllers for the backlights to dim them during the pixel change period, leading to added complexity and expense.

Moreover, whereas CRTs were driven by analog signals, LCD displays usually are driven by digital signals. The resulting delay between the time that a frame is sent to the display and the time that frame is displayed can be a significant problem with LCDs because optical stimulators generally require exact timing between application of the stimulus and triggering of the response measurement. In fact, the standards for latency in some ERG measurements have had to be modified to deal with this effect and this issue has created difficulties in comparing results from the two systems and between measurements made using different LCD displays. Again, there is no user control of the wavelengths of the illumination; the LCD manufacturer picks the filters to apply to the white backlight to generate the display colors. An additional concern is that the light from LCD displays is polarized (as opposed to that of CRT based displays) and this may have some influence on the effect of the stimuli.

It is also known to project images directly on to the retina in the fields of information technology and entertainment where wearable displays have been developed. These displays generally use as the image source a compact LCD display and have the characteristic limitations of this technology as described above.

Many of the LCD problems also apply to the newer organic liquid crystal (OLED) displays with the exception of the light leakage problem which does not occur since the output of each pixel (LED) is directly controlled.

It has been proposed to use arrays of massed LEDs as optical stimulators. This allows spectral control (within practical limits of mounting hundreds of LEDS) and also allows for true impulse stimuli. A disadvantage of such LED arrays, however, is a lack of flexibility in the patterns produced since the LEDs are in fixed locations. In addition, the LEDS are seen as discrete light sources by the eye, which does not fit with most of the assumptions about the properties of optical stimulators.

A further limitation is that CRT and LCD displays and custom LED arrays are viewed at a distance by the patient and so the environmental and experimental conditions, ambient light, display luminance, distance etc., need to be controlled carefully because the illuminance of the stimuli on the retina depends on all these factors, plus the anterior clarity of the subject's eye and, last but not least, on the pupil diameter of the subject's eye.

In general, therefore, none of the above-described commercially available displays is entirely satisfactory for use optical stimulators:

It has been proposed to use, as another alternative, micro-mirror devices in optical stimulators. These have usually tried to take advantage of a commercially-available projector incorporating the micro-mirror device, typically known as a DLP (Digital Light Projector). A problem has been that these devices were designed to display video signals and use RGB lighting. This meant that there was a fixed frame rate, with the stimulus on for the full frame and no fine control over illumination. Also the commercial controllers made compromises with the detailed timing, which made their use as an optical stimulator very difficult. Typically, the incoming video stream is digitally adjusted to provide smooth video images and gamma values adjusted to replicate conventional displays.

DLP projectors have been investigated as optical stimulators, both in Maxwellian view and as viewed in front or back projection. Researchers report limitations caused by using conventional video drivers. For example, Packer et al. [Packer] disclosed a three DLP commercial projector but commented that they encountered limitations imposed by the video driver, specifically the limit on temporal performance imposed by the 63 Hz refresh rate.

Kuchenbecker et al. [Kuchenbecker] disclosed a single chip DLP projector modified to allow for nine LEDs, but which still used a VGA based video stream. Consequently, it too would be susceptible to the temporal limitations encountered by Packer et al.

Much the same applies to a DLP projector marketed as the PICO™ projector by Texas Instruments. It would not be entirely satisfactory for use in an optical stimulator because its frame timing and illumination periods did not have a regular output with an extra-long sub-frame occurring at the end of the nominal 60 Hz video input frame and for which the illumination was actually turned off.

Other limitations of known optical stimulators will be apparent from the following discussion of electroretinograms (ERG) and Visually Evoked Potential (VEP) systems for assessing functionality of the retinal and/or other parts of the visual system. As mentioned above, they employ optical excitation of a portion or portions of the retina and an electrical probe attached to the skin near the eye (in the case of ERG) or the rear of the head (in the case of VEP) or elsewhere to sense resulting electrical nerve impulses representing the processing and transport of information between the retina and the brain.

These impulses are generated by the rods and the cones and their associated nerve cells. These two sources have different spectral sensitivities and different dynamic responses, enabling their respective contributions to be distinguished. For cone assessment, a source near the photopic peak sensitivity wavelength of 555 nm is desirable. Moreover the dynamic response of cones is much faster, extending beyond 30 Hz.

One purpose of the ERG and VEP is to establish the retinal functionality at each location on the retina. The retinal cone density is non-uniform, being high in the central foveal region and lower in the peripheral regions. In order to obtain satisfactory signal levels in the peripheral regions, the spatial resolution demanded is reduced; the global objective is to create a cone map such that each retinal area to be sampled has approximately the same number of cones. A standard arrangement has each area being in the shape of a hexagon and all hexagons being sized according to cone density and clustered to fill all the available area leaving no gaps.

ERG/VEP visual stimuli may be classified as "pattern" or "multifocal". The "pattern" type uses a systematic fixed pattern such as an alternating checkerboard or parallel bars. This measures the ganglion cell response. The multifocal type generates pseudo-random sequences both in terms of spatial and temporal arrangement and is capable of generating a spatial sensitivity profile or map across the retina. In various embodiments, an ERG system may use either type of stimulus and, for convenience, in this specification the term "pattern" may be used for both according to context, on the basis that each of the multiple points used in multifocal ERG/VEP constitutes a pattern. The custom focal ERG/VEP can address the response of a specified local retinal region. A typical stimulation arrangement uses an m sequence. The pattern stimulation arrangement uses cyclic summation, a technique of alternating stimulation where the frame cycle rate can be varied.

Where the ERG is captured using a single collection sensor, the location determination is made by directing light of known power to the required retinal location, where it should have a spatial dimension no larger than the required retinal resolution. An alternative to sequential scanning is the use of sequential multiplex projection, wherein various coded combinations of retinal areas are excited in sequence; during the subsequent processing, the contribution of each retinal area can be decoded. This technique is a form of multifocal ERG.

The multifocal method is analogous to the complement of pattern imaging where the target is uniformly illuminated but the image is captured using a single optical detector preceded by a temporal sequence of coded masks in a conjugate image plane. Multiplex methods generally result in a better image quality where the non-multiplexed limitation is the noise level of the sensor.

Previously known multifocal ERG art used coded images displayed on CRT's, or more recently LCD screens upon which the patient was required to stare for typically 10 minutes. In addition to the problem of patient movement, the displays do not generate as much light as is desirable for ERG purposes. Moreover, the amount of light captured by the eye is dependent on the pupil size, a quantity that varies with ambient light level and between people. Furthermore, the spectra of the three light channels (RGB) LCD screens and CRT monitors are satisfactory for visual displays but suboptimum for the purposes of ERG collection. In addition, the dynamic response of LCD displays, which may be fully adequate for consumer purposes, is a limiting factor for ERG investigations where greater speed can be useful. Finally, as mentioned above, the light from LCD displays is partially polarized rather than unpolarized that is preferable.

The capture process is very time consuming and makes it difficult or almost impossible to assure that the patient fixates consistently, a condition for avoiding uncertainty in the location on the retina.

As discussed above, the spectral content of the light emitted by the screens is controlled by the manufacturers of the screens and is, in many cases, non-ideal for stimuli for the retina and nerves and can vary from screen to screen. There are also issues in the way the frame is changed from one frame to the next. In a CRT the electron beam scans rows across the screen moving row by row from the top to the bottom. The phosphors are excited but then start to fade. There is also a flyback delay where the beam returns to the top. In a LCD screen the pixels do not change all at once either but are addressed sequentially in rows across the screen, creating a vertically moving band as the pixels change (quite slowly—over a few milliseconds) on the screen. These imperfections may be acceptable for video and computer monitor viewing but are not acceptable for some stimulus/response measurements. The subject also needs to be positioned in front of a screen and control of the ambient light levels and avoidance of distractions in the room is important. The luminance of screens is also an issue and in some cases can limit the experiments/assessments where more luminance would be desirable, i.e., to enable a faster flash or a brighter stimulus pattern.

A secondary area of interest has been in instrumentation capable of directly observing the stimulus on the retina. Various experiments have been tried using SLO (scanning laser opthalmoscopes) instruments to generate a stimulus and then observe its effect on the retina using laser imaging.

SUMMARY OF INVENTION

An object of the present invention is to at least mitigate the deficiencies of such known optical stimulators, or at least provide an alternative.

Our Approach

To achieve these goals is the objective of this 'project'. The first and most important step is to separate the generation of the image from the generation of the illumination. Unlike CRT, LCD and OLED displays or LED arrays where the image is created along with the illumination, the new optical stimulator uses a digital micro-mirror device (DMD) to generate the image pattern and separate illuminator(s) such as LEDs, lasers or continuous white light sources to illuminate it and thus generate the optical stimuli seen by the subject.

DMDs (digital micro-mirror devices) comprise an array of steerable micro-mirrors, each of which can be in an "on" state or an "off" state. There are a number of such devices available, ranging from 480×320 mirrors to 1928×1024 mirrors. The most common uses for these devices are in projectors and for digital cinema at the high end. These devices typically use a video input and are geared to consumer and general commercial applications.

The new visual stimulator can be used in various modes; one mode is to project the images onto a screen, either rear or front screen projection, and have the subject look at that screen and another mode is to project the image onto the retina directly through the pupil. In the chosen implementation the new visual stimulator has been used in the direct projection onto the retina mode. It has been integrated into an ophthalmoscope and uses Maxwellian optics to project the patterns directly onto the retina. This can be done using true Maxwellian projection where the projected image of the mirror device is positioned in the plane of the entrance pupil of the subject's eye or pseudo-Maxwellian where the image is at the corneal surface (in order to minimize the size of the corneal reflection). The projection method has the advantage that the area of the retina illuminated by the DMD can be varied and thus the spatial resolution of the images changed to be appropriate for the required stimulus.

According to a first aspect, there is provided a system for use in assessing functionality of at least a part of a visual system of a subject, the system comprising:

at least one digital micro-mirror device (DMD);

a controller for controlling the DMD to configure the micro-mirrors to form a stimulus pattern;

light input means for directing light to the DMD;

optics positioned and configured to receive light reflected from the patterned micro-mirrors and direct the reflected light to the eye of the subject to image the stimulus pattern onto the retina as a stimulus image; and a sensor unit for providing an output signal indicative of a response of at least part of the visual system of the subject evoked by the stimulus image;

at least one processor for processing the output signal in relation to the stimulus pattern to enable an assessment of the functionality of said at least a part of the visual system.

According to a second aspect, there is provided a method of assessing functionality of at least a part of a visual system of a subject, comprising:

using a controller to configure micro-mirrors of a digital micro-mirror device (DMD) (108) to form a stimulus pattern;

directing light to the DMD (108);

using optics (104) to receive light reflected from the patterned micro-mirrors and direct the reflected light to the eye (120) of the subject (125) to image the stimulus pattern onto the retina as a stimulus image; and using a sensor unit (106) to provide an output signal indicative of a response of at least According to a third aspect, there is provided an optical stimulator for providing light for optical stimulation of a retina of a subject, comprising:

a micro-mirror device (DMD) (108) comprising an array of micro-mirrors;

a controller (110) for controlling the DMD (108) to configure the micro-mirrors to form a stimulus pattern; and light input means (100) for directing light to the DMD (108);

the arrangement being such that light reflected from the patterned micro-mirrors can be directed by juxtaposed projection optics (104) to the eye to form an image of the corresponding stimulus pattern onto a retina of an eye (120) of a subject (125).

According to a fourth aspect, there is provided a system for measuring the response of a retina and/or other part of a visual of a subject to light, the system comprising: a first light source; a digital micro-mirror device (DMD) for creating a coded image pattern; optics for relating the light source, the DMD, and projecting the coded image pattern onto the retina of the eye; an electroretinogram (ERG) sensor for measuring a response of the eye to light, the ERG sensor producing electrical signals based on the response of the eye; and at least one processor coupled to the DMD and the ERG sensor, the at least one processor configured to: control the DMD to generate the coded image patterns; and process the electrical signals produced by the ERG sensor.

The foregoing and other objects, features, aspects and advantages of the present invention will become more apparent from the following detailed description, taken in conjunction with the accompanying drawings, of specific embodiments of the invention, which are described and illustrated by way of example only.

BRIEF DESCRIPTION OF DRAWINGS

In the drawings, identical or corresponding elements in the different Figures have the same reference numeral.

DESCRIPTION OF SPECIFIC EMBODIMENTS

Figure 1:
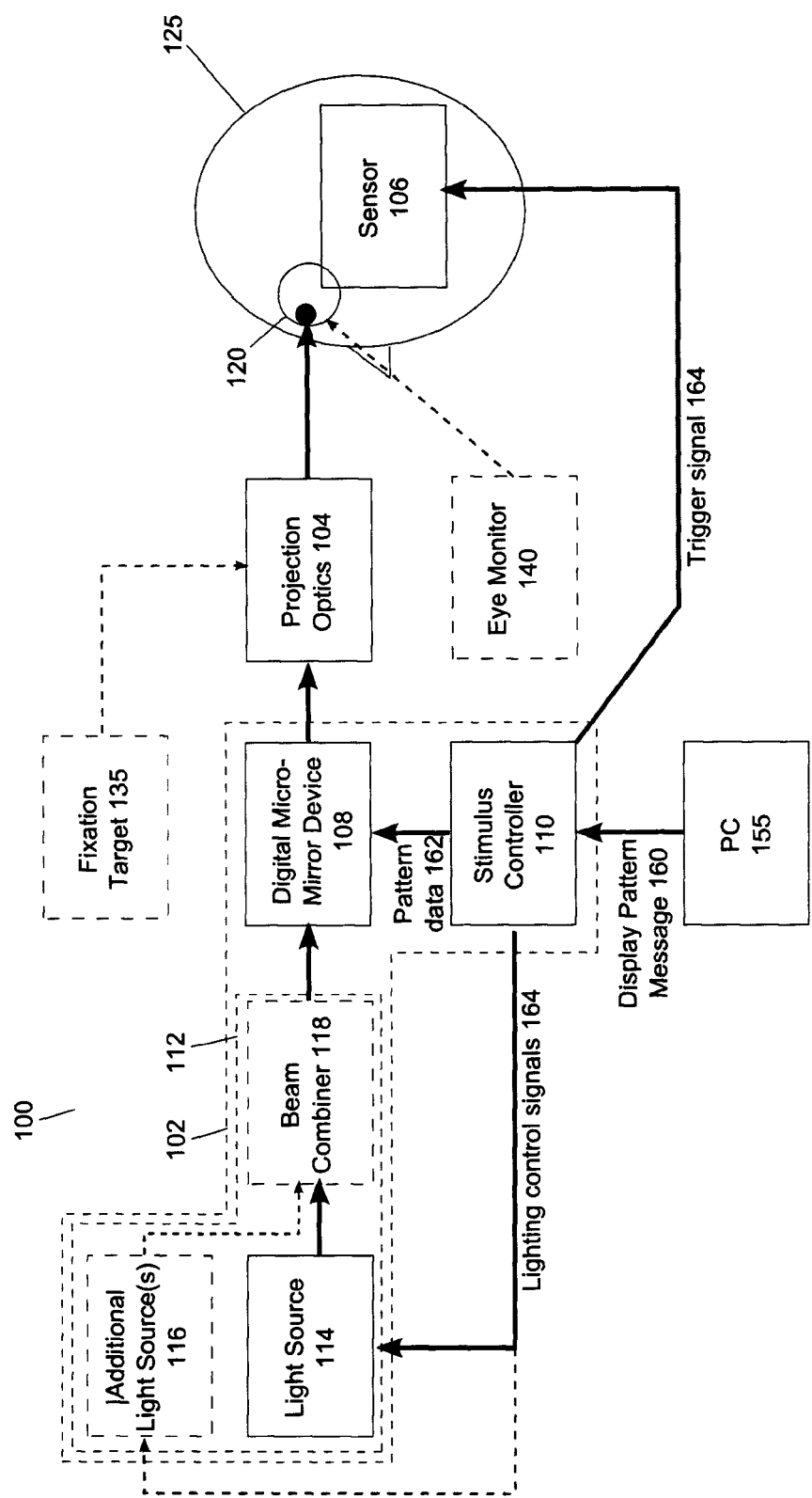
FIG. 1 is a block schematic diagram of a system for assessing retinal function including an optical stimulator embodying one aspect of this invention.

FIG. 1 illustrates a specific embodiment of a system 100 for assessing retinal functionality. The system 100 comprises an optical stimulator 102 (was 105, 145, 150, 110) for producing one or more stimulus patterns to input light, projection optics 104 (115) for projecting images of the stimulus pattern(s) onto a retina of an eye 120 of a subject 125 and a sensing unit 106 (was 130) for sensing responses evoked by the stimulus images.

As shown, the optical stimulator 102 comprises a DMD device 108 having an array of micro-mirrors (not shown) which can be switched individually in response to control signals from a controller 110. Input light for irradiating the array of micro-mirrors is provided by a light input unit 112 which comprises a light source 114 (was 105), for example a LED, coupled to the DMD device 108. Optionally, the light input unit 112 may comprise one or more additional light sources for emitting light having a different wavelength to that emitted by light source 114. In FIG. 1, such an additional light source 116 is shown in dashed lines with a beam combiner 118, also shown in dashed lines, for combining light from both light sources for application to the DMD device 108.

In some embodiments, light source 105 may be spectrum optimized for use in electroretinograms. For example, in some embodiments, light source 114 emits light with a wavelength near 555 nm.

Sensing device 106 is used to sense the response of the retina to light from light source 114. Light incident upon the retina stimulates electrical nerve impulses that can be monitored locally using electrodes (e.g., using electrodes on the eye or neighbouring skin, as in ERG) or, after being transported through the optic nerve, more remotely using electrical sensors located at the rear of the head. This latter technique is called the Visually Evoked Potential (VEP). This, in some embodiments, sensor 106 comprises an ERG sensor. In some embodiments, sensor 106 comprises an VEP sensor. In yet other embodiments, sensor 106 might comprise a plurality of EEG sensors.

Optics 104 (was 115) can be implemented using commercial optics such as those marketed by Texas Instruments as Projector™ optics, along with additional lenses. For example, the commercial Pico projector optics can be used basically unmodified, but with a 20-30 mm FL plano-convex lens directly in front of its final projection lens and a different LED source. In some such embodiments, system 100 includes LEDs and a collimating lens, then beam combiners for the LEDs followed by a lens and mirror to illuminate the DMD at 24 degrees, a projection lens, followed by another lens. In some embodiments, to be described later, these components are placed in an ophthalmoscope system at the place where the LEDs reside using all existing optics but with the LED collimator lens removed.

Figure 2:
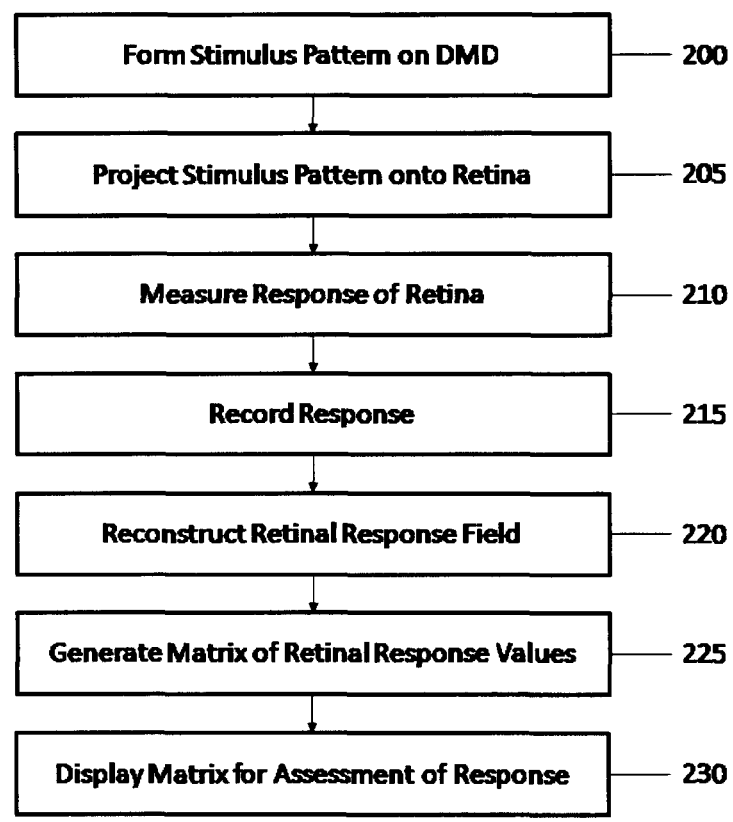
FIG. 2 is a simplified flowchart illustrating operation of the system of FIG. 1.

FIG. 2 illustrates very generally use of the system of FIG. 1 to produce so-called multi-focal stimulus images on the retina.

In various embodiments, system 100 operates as follows. The computing device 155 transmits a message to the stimulus controller 110 which sets the DMD pattern and then sets the LED of light source 114 to emit for a specified duration and intensity. The electrical response from ERG sensor 106 is recorded. Computing device 155 then sets the next DMD pattern and the process is repeated. This sequence is repeated a number of times until the sample set is large enough to reconstruct the desired retinal response field with the desired spatial resolution. Computing device 155 then processes all the responses accordingly and creates a matrix of retinal response values. This can be displayed on for example, the display of computing device 155, in a variety of visual formats such as intensity or colour.

At 210, the response of the retina of patient 125 is measured. In various embodiments, the response of the retina is measured indirectly by measuring the response of the optic nerve. In some embodiments, this is accomplished through the use of an ERG sensor attached to patient's 125 skin to sense the electrical impulses generated by the optical nerve.

In various embodiments, images of stimulus patterns are projected in sequence onto the retina and the response of the retina to each image pattern is measured. Accordingly, it should be understood that the flow chart diagram of FIG. 2 is intended to illustrate the overall method and should not be interpreted as illustrating a particular series of events. Accordingly, the events represented by 205 and 210, as well as other elements of FIG. 2, may overlap in time.

At 215, the response is recorded. In some embodiments, computing device 155 records the response by processing the electrical signals generated by ERG sensor 106 and storing them on a storage device to which it is coupled.

At 220, the retinal response field is reconstructed. In various embodiments this is done based on the samples that have been collected up that point for the particular retina being studied. For example, in some embodiments, computing device 155, uses the samples stored on the storage device to reconstruct the retinal response field.

At 225, a matrix of retinal response values is generated. In some embodiments, computing device 155 displays the generated matrix in one or more of a variety of possible visual formats. For example, in some embodiments, computing device 155 displays the matrix values on the display where the intensity at a particular position represents the response value. In other embodiments, color values are used to represent response values.

The configuration and operation of the DMD device and controller 110 will now be described with reference to FIG. 3. The micro-mirror array includes local memory (not shown) for storing information for the state of each individual micro-mirror. The DMD controller 110 comprises its own memory 174 for storing data for constructing each stimulus pattern, an input-output interface 170 for communicating with the external computer 155 (see FIG. 1) using a command stream protocol and an output interface 162, 164, 166 for outputting various control and timing signals as will be described in more detail later.

Figure 3:
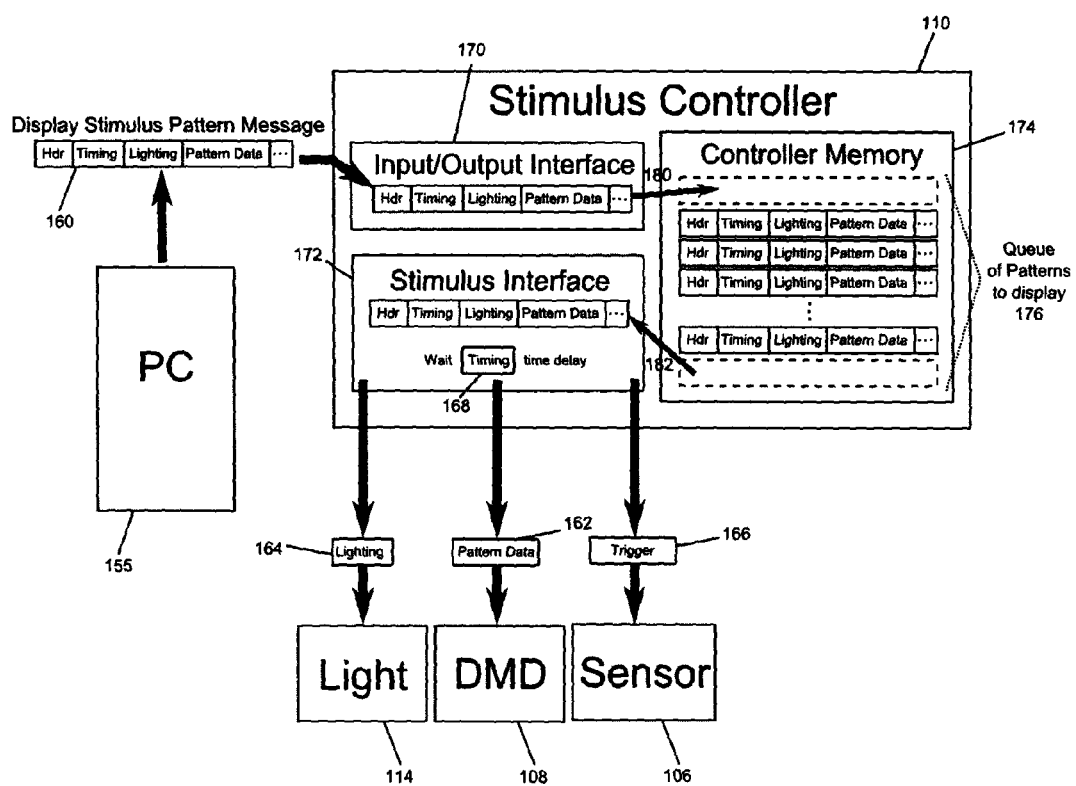
FIG. 3 a block schematic diagram illustrating in more detail a micro-mirror device and its controller.

Referring now to FIG. 3, in the example shown, the master PC 155 sends a display pattern message 160 to the stimulus controller 110. The stimulus controller 110 receives and interprets the received message in its input-output interface as a pattern message to be display by the DMD 108. The controller 110 therefore extracts the pattern display information and enqueues 180 it in a first-in-first-out (FIFO) queue 176 which is contained within local memory 174 on-board the controller 110. The controller also contains of a stimulus interface module 172 which outputs data to physical stimulus devices which include the DMD 108, lighting 114, and measurement sensors 106. The stimulus interface continuously scans the FIFO queue 176, and when it contains stimulus patterns to be displayed it dequeues 182 the next pattern from the queue 176 and extracts the timing 168, pattern 162, lighting 164, and triggering 166 information.

Timing information 168 defines how long a given stimulus pattern should be displayed for, defined in microseconds or in controller clock ticks. Once this timing 168 elapses, the stimulus interface 172 dequeues 182 and displays the next pattern from the queue 176.

Pattern information 162 contains the desired state of each of the micro-mirrors in the DMD 108 on a mirror-by-mirror basis. This pattern information can be encoded in a variety of different formats, and it is the stimulus interface 172 which decodes and interprets the pattern as received from the PC 155, and translates it into the format expected by the DMD 108 to allow for pixel level control of each individual micro-mirror.

Lighting information 164 contains parameters for the illumination system. In the case of light emitting diodes (LEDs) for example, lighting 164 includes pulse-width-modulation (PWM) and current settings. The stimulus interface 172 interprets this information and configures the lighting hardware for the duration of the pattern stimulus.

Finally, triggering information 166 contains any triggering instructions which should be output from the controller 110 to inform connected sensor hardware 106 of when the display pattern has been updated for synchronization purposes.

Figure 4:
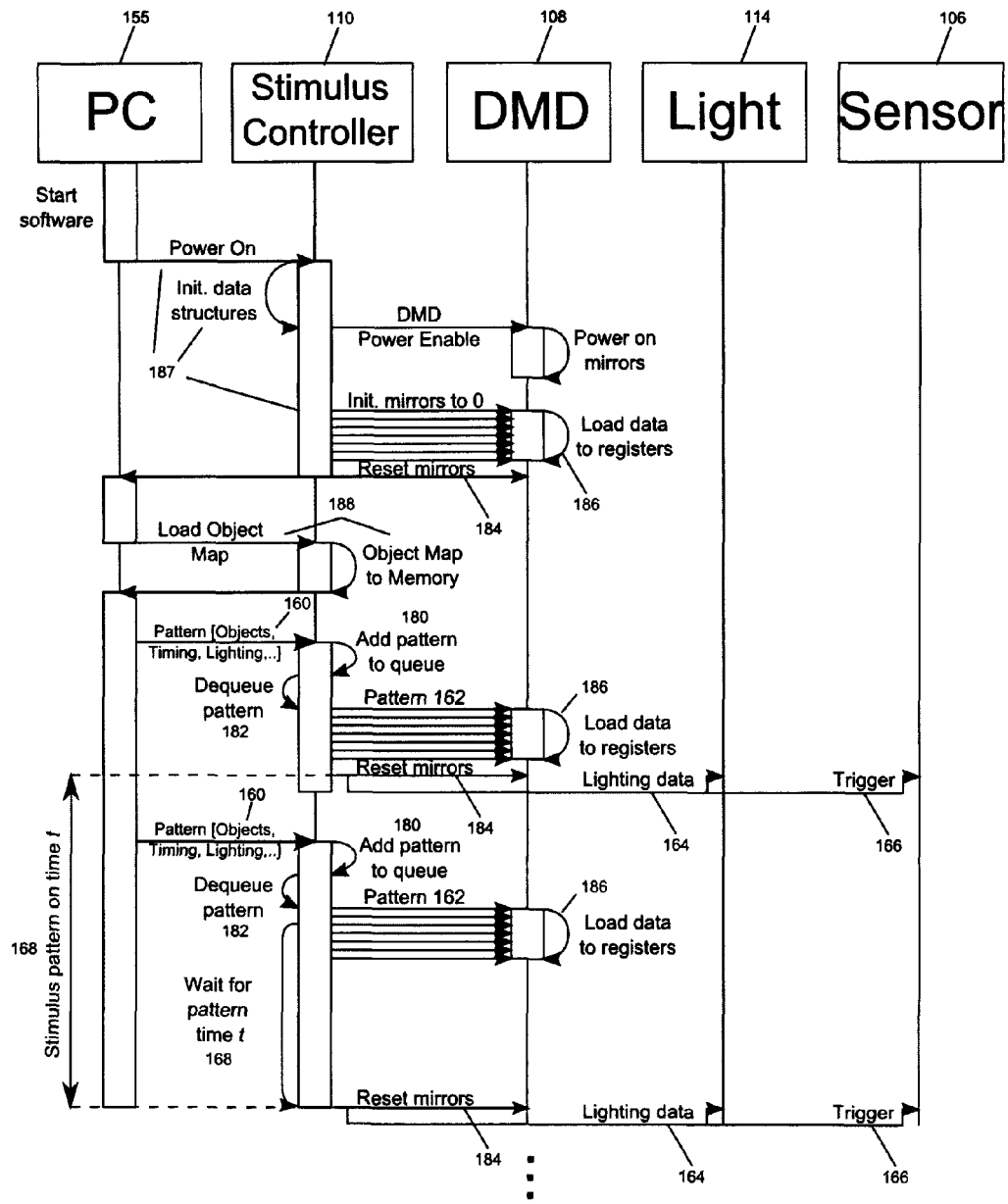
FIG. 4 is a sequence diagram illustrating overall operation of the optical controller of FIG. 3.

Referring now to FIG. 4, the command stream between the PC 155 and stimulus controller 110 is a flexible protocol for transferring data to and from the stimulus controller. In the current implementation it uses a USB2 interface for the PC 155 to communicate with the controller 100, which is implemented on an FPGA. The command stream uses a variety of messages to drive the stimulator. These messages include the ability to reset the controller, load images to be displayed, and to control lighting conditions and triggering to external equipment such as ERG sensors. A number of these messages in a typical sequence of operations from initial startup to the displaying of stimulus on the DMD 108 are described with reference to FIG. 4.

The PC 155 software begins, and sends the power on message to the stimulus controller 110. The controller 110 initializes data structures 190 and the DMD 108 mirrors to default positions (e.g. to the off-state.) Once the data is loaded into the DMD registers the DMD 108 is reset 184, and all mirrors simultaneously move to their new positions. FIG. 4 shows the loading of an inline object map 188, which is stored in memory 174 on the DMD controller 110. Now that an object map is loaded onto the DMD controller 110, the PC 155 sends an image message 160 to the controller 110. The pattern data 162 is extracted from the message, along with the lighting 164, timing 168, and triggering 166 properties, which are stored in a queue 176 to be displayed on the DMD 108 sequentially. As pattern data appears in the queue, the DMD controller 110 dequeues the next frame 182 and loads the data into the DMD 108 sequentially 162. In the present example for an object map, each object map image command contains a bit for each object defined in the preloaded object map (typically 256 objects) and the bit indicates whether the object is to be illuminated for this image. For bitmap images, several bitmaps can be stored and indexed on the FPGA controller 110 in advance, and a bitmap image command indicates which of the stored bitmap images to display. The image data is loaded to the DMD registers 186. Each mirror has associated with it a binary register which determines which position it will be in when next reset. Once loaded into DMD registers, the reset mirrors signal 184 is sent to the DMD, and all mirrors simultaneously move to their new positions. Synchronous with the mirror update, lighting conditions (such as LED current and PWM settings) are changed 164 to reflect the desired properties in the display pattern message 160, as well as a trigger signal 166 is sent to sensor electronics 106. The procedure of the PC 155 sending stimulus patterns 160 to the DMD controller 110 is repeated, and images are continually added to the queue 180. The DMD controller 110 will dequeue images from the queue 182 as they become available, and load the data to the DMD registers 162, 186. However, the controller 110 will not reset the DMD micro-mirrors 108 until the specified amount of stimulus time has elapsed 168 as specified in the image frame message 160. This ensures that patterns are displayed for very precise amounts of time as specified in the USB2 messages and are not governed by frame rates as traditional display controllers would be.

The sequence as described in FIG. 4 continues for as long as the PC 155 contains patterns for the given procedure. The PC 155 will generate and send the stimulus patterns 163 faster than the stimulus controller 110 can execute them so there is a flow control mechanism in place where the stimulus controller 110 sends a message over the data interface or uses a hardware signal to indicate that the queue is at an upper limit mark, thus ensuring that it never overfills the memory allocated for the queue 176. The procedure by which the stimulus controller 110, or more specifically the input-output interface 170, enqueues stimulus patterns when pattern messages 160 are received from the PC 155 is described with reference to FIG. 5. The input-output interface 170 begins by waiting for a new message to arrive on the USB2 interface 250. When a message is received, it is decoded and handled appropriately based on its type. The current example shows the flow of handling a pattern stimulus message type 252. Other message types are handled by similar program blocks 254, not shown here. When a pattern message 160 is received, the current size of the pattern queue 176 is first checked 256. If the queue size is over the upper limit mark, a flow control XOFF message 260 is sent to the PC 155 to indicate that no more stimulus patterns should be sent since the queue 176 is nearly full. If the queue 176 is not full, the pattern is added to the queue 180 and the input-output interface 170 waits for another message 250. Otherwise if the queue is full 264, the pattern is simply discarded.

Figure 5:
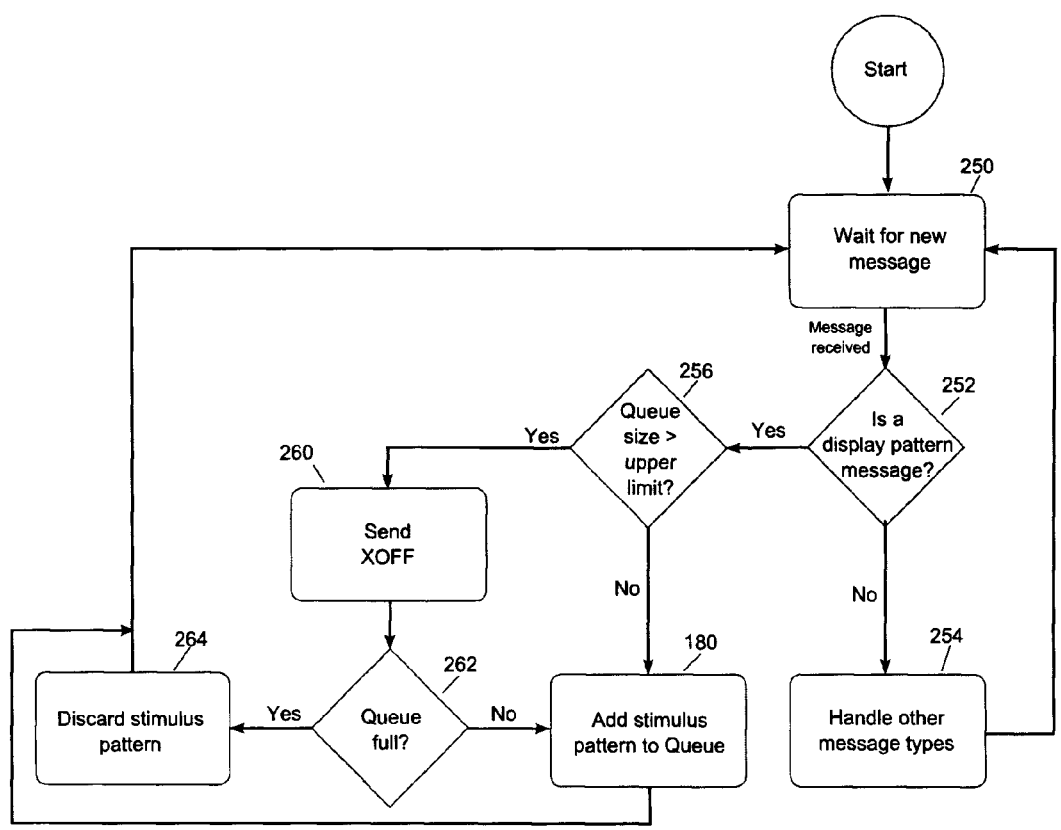
FIG. 5 is a flowchart illustrating loading of stimulus pattern data into the controller of FIG. 3.
Figure 6:
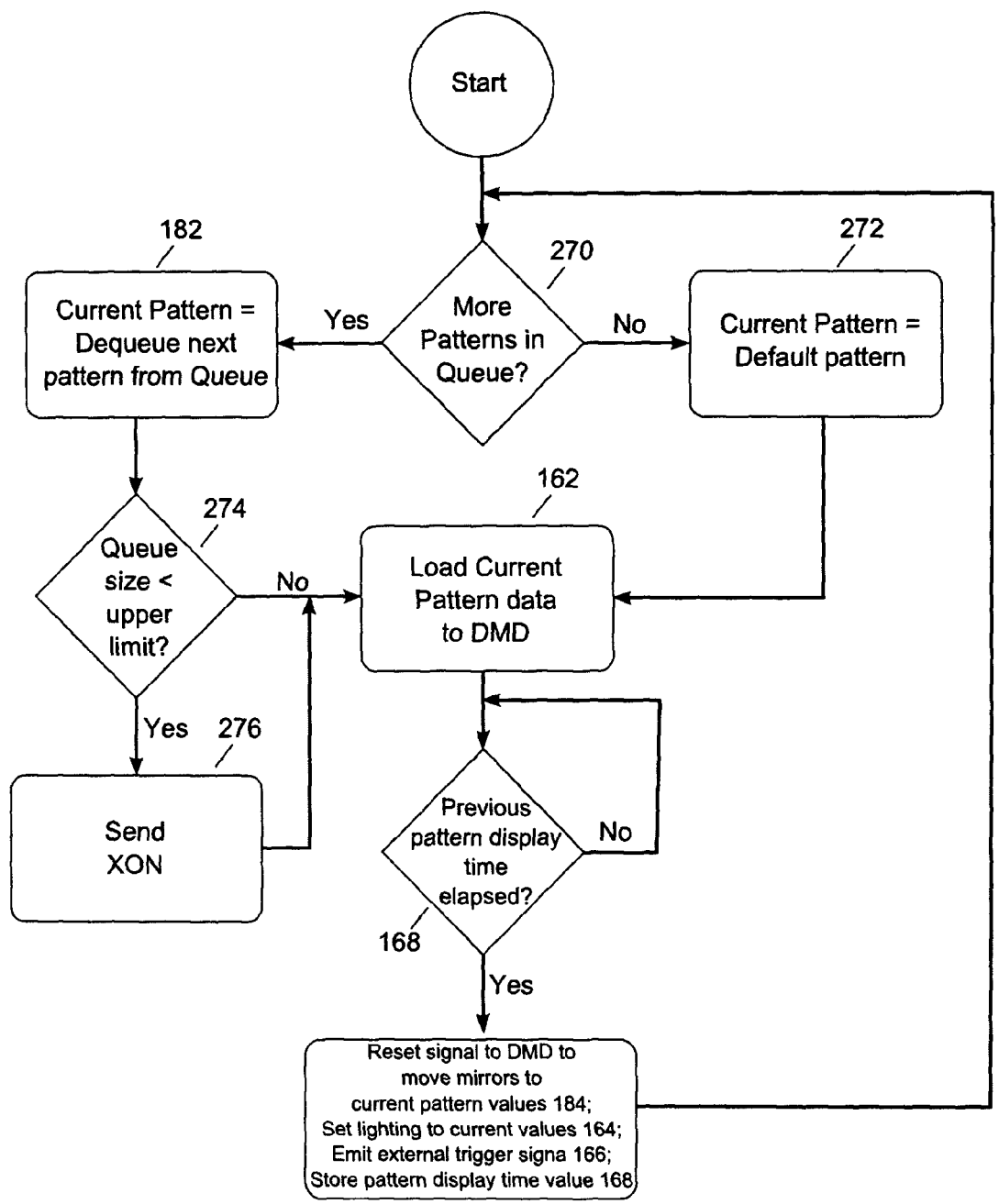
FIG. 6 is a flowchart illustrating operation of the controller of FIG. 3 to generate stimulus patterns for projection onto the retina.

In parallel with the input-output interface 170 operational loop as described in FIG. 5 is the stimulus interface 172 operational loop which is described with reference to FIG. 6, in which the stimulus controller 110, or more specifically the stimulus interface 172, reads available patterns from the pattern queue 176 and drives the DMD mirrors 108 to the state represented by each pattern in the queue 176 sequentially. If patterns exist in the queue 270, the next frame is dequeued 182. If after dequeueing the pattern the queue size is below the upper limit mark 274, the flow control XON signal 276 is sent to the PC 155 to let it know that more patterns can now be accepted. The image is then loaded to the DMD 108 with a sequence of signaling instructions 162. If no more images are in the queue 176, a default image is sent to the DMD 272, which could for example be all mirrors set to the off-state position. The stimulus interface 172 then waits for the desired amount of pattern display time 168 from the previous stimulus pattern to elapse to ensure that each pattern is displayed for the correct amount of time as specified in the pattern message 160. After the pattern display time 168 has elapsed, the controller 110 finally resets the DMD 108, thus moving the mirrors to their new positions 184, while simultaneously changing lighting settings 164 and triggering an external sensor 166.

The object map frame command for a typical installation is about 70 bytes in length. At 6800 frames/sec this would need about 500 KB/sec for a data stream capability. A USB2 interface at a nominal 480 Mb/sec to a chip creating a parallel interface to the FPGA can effectively deliver about 10 MB/sec of data. The frame command stream is thus completely capable of driving the stimulus controller at full frame speed.

Figure 7:
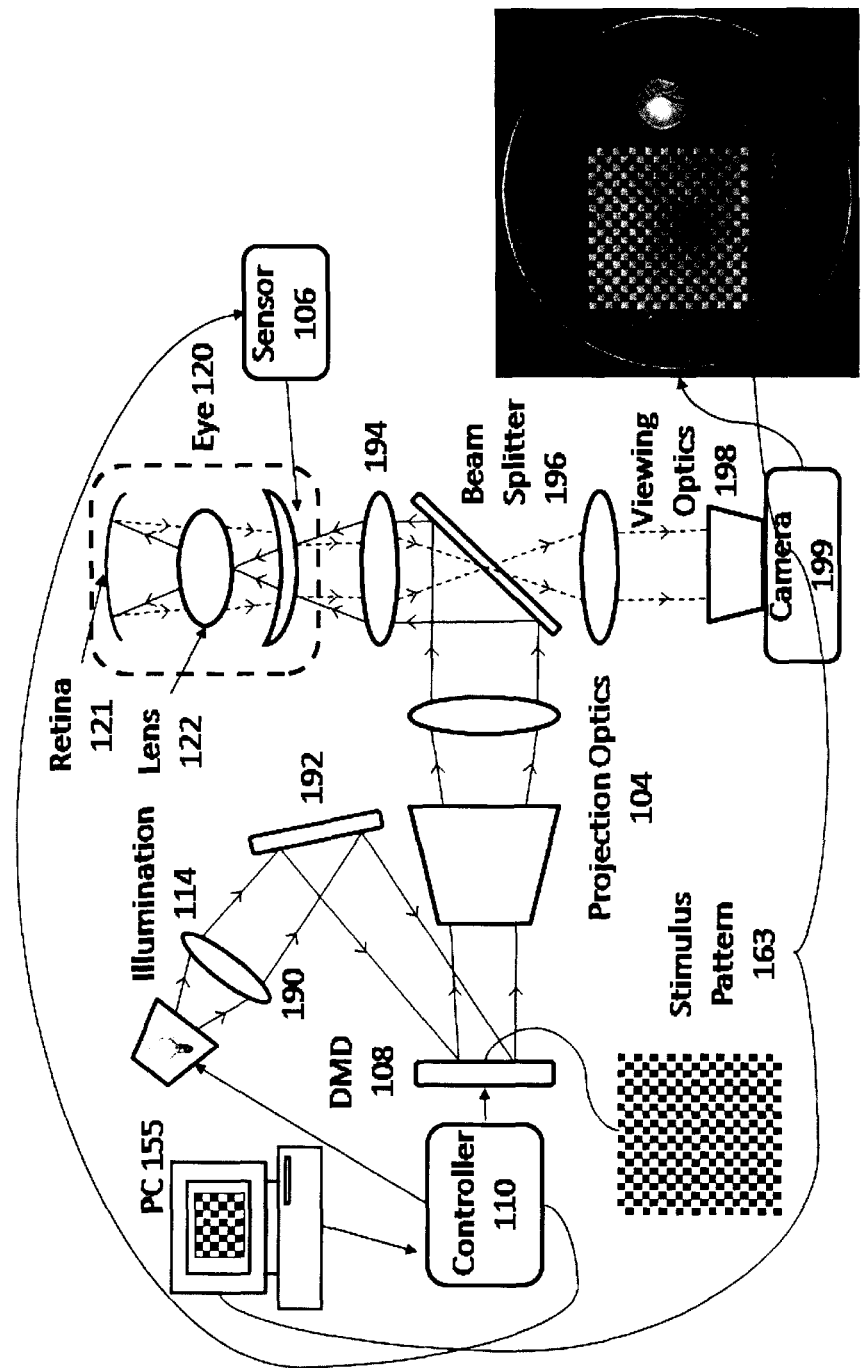
FIG. 7 is a schematic diagram of an embodiment of the invention comprising an optical stimulator combined with an ophthalmoscope.

FIG. 7 illustrates schematically integration of the stimulus controller of FIGS. 1 to 6 into an ophthalmoscope. The DMD acts as a projector and uses Maxwellian optics to project the stimuli onto the subject's retina. The projector beam is reflected off a beam splitter into the eye and the viewing path also uses the same beam splitter but in direct transmission. The stimulus projector can act as a very flexible fixation target generator for normal ophthalmoscope use.

Figure 8A:
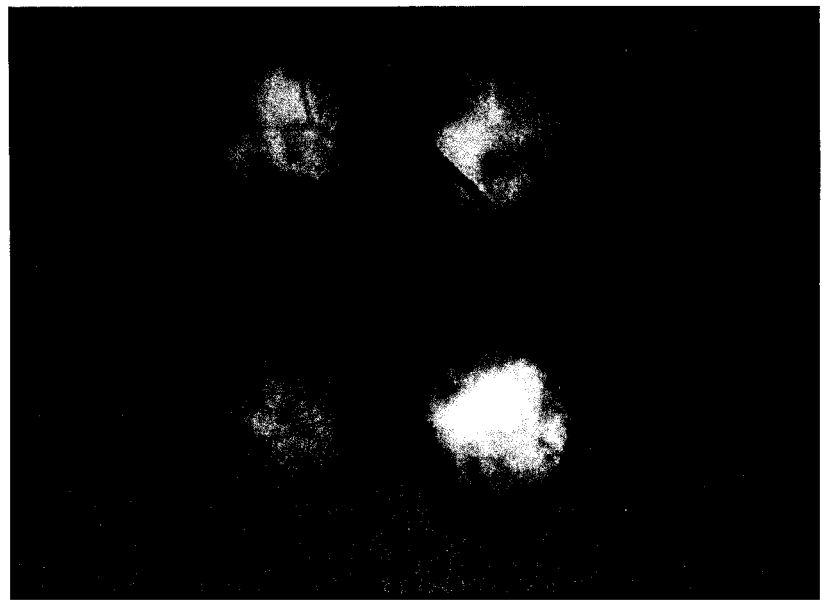
FIG. 8A illustrates images of four stimulus patterns on the retina of a subject.
Figure 8B:
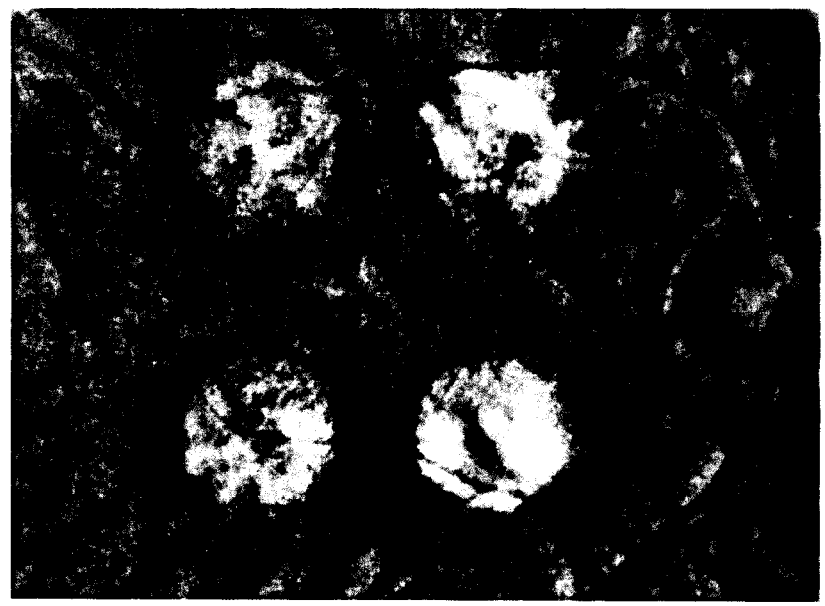
FIG. 8B illustrates images of four stimulus patterns similar to those in FIG. 8A but with choroidal illumination.

An advantage of this integration is that the stimuli as projected on the retina can be imaged via the digital camera in the ophthalmoscope. The wavelength capability of the combined instrument ranges from 360 nm to 1000 nm with reduced transmission and detectability at the extremes. This means that stimuli can be projected using visible light of various wavelengths with intervening frames using NIR light to allow visualization of the vasculature of the retina and the stimuli at the same time, thus allowing accurate registration of the stimuli to the retina and any associated pathology for which functional testing is to be performed. As a second approach, choroidal images can be acquired along with the projected stimuli to allow for the registration. The choroidal images are generated by trans-scleral illumination by NIR light. For details of a method of doing so the reader is directed to commonly owned international patent application number WO 2011/160238 A1 the entire contents of which are incorporated herein by reference. FIG. 8A shows the digital camera image of four circular stimuli projected onto a human retina using green light. In FIG. 8B the same stimuli are shown but now with the choroidal vasculature made visible using the trans-scleral illumination.

The DMD based optical stimulator has been integrated into two ophthalmoscopes. One ophthalmoscope has masks in the optical path to the digital camera that are designed to remove the corneal reflection of the illumination, which is sent through the center of the eye in this design. This method of operation is very suitable to work with the new stimulator since the DMD projector can be set up to come to a minimum area or waist at the cornea so that all the light enters the pupil and none hits the iris, even for a small pupil. The corneal reflection of this is then masked prior to the digital camera. This approach allows the use of the default illumination of the ophthalmoscope in addition to the optical stimulator.

The optical stimulator has also been integrated into an ophthalmoscope that does not have masks in the optical path to the digital camera. In this case crossed polarisers are used to remove the corneal reflection when imaging the retina. The projector can now be used in a proper Maxwellian fashion with the focus in the plane of the center of the lens since the need to minimize the area on the cornea is less strict. The stimuli in this case will be mostly polarized light and the results can be compared with those obtained using the first or masked model system where the stimuli are unpolarised.

An optical schematic of a possible implementation which focuses the pattern stimulus 163 from the DMD 108 onto the retina 121 is shown in FIG. 7. The illumination source 114, which could comprise of LEDs of varying wavelengths, is collected with suitable lenses 190, and directed towards the DMD 180 at the correct angle of 24 degrees with a mirror 192. Light from DMD mirrors in the on-state, represented by the stimulus pattern 163, are directed towards projection optics 104 and reflected off of a beam splitter 196. Reflected light is focused onto the eye lens 122 using a final lens element 194 and inserted into the eye in Maxwellian fashion. The stimulus pattern 163 forms an image on the retina 121, where it produces an response 210, 215 which can be recorded by sensors 106. A portion of the light from the stimulus is also reflected from retinal tissue, and re-enters the optical system through the lens 194. This light is transmitted through the beam splitter 196 on a separate path from the DMD stimulator, and is collected by viewing optics 198 and focused onto a camera 199. As a result, the pattern stimulus 163 as first generated by the PC 155 and displayed on the DMD 108 is effectively projected directly onto the retina 121, and simultaneously observed by a camera 199.

Various modifications to the above-described embodiments may be made without departing from the scope of the present invention. Thus, some embodiments of system 100 may also include a fixation target 135 for patient 125 to focus their gaze upon. In some embodiments, a fixation target may be in the form of a point such as a bright spot on a dark background or vice versa. Alternatively, in other embodiments, fixation target 135 may be in the form of an extended image having an evident centre such as a cross. The fixation target may be a separately arranged viewing screen or it could be integrated with the DMD projection. In some embodiments, the colour of the fixation target or its background is chosen to ensure least interference with the ERG process.

Various embodiments also include an eye monitor 140.

In various embodiments, system 100 may comprise a computing device 155. In some embodiments, computing device 155 can be any appropriate computing device such as for example but not limited to a general purpose computer such as a laptop, desktop or tablet computing device. In other embodiments, computing device 155 can be an integral component of system 100. In various embodiments, computing device 155 includes, for example, one or more processors, memory, one or more input devices and one or more output devices, such as, for example, a display. In addition, in some embodiments, computing device 155 is coupled to sensor 106 and processes the signals received therefrom. In addition, computing device 155 may record the processed signals in its memory or a storage medium to which it is coupled.

In some embodiments, one or more devices may be used for processing data received from sensor 106 and one or more devices may be used for controlling various components of system 100. In some embodiments, a field-programmable gate array (FPGA) is used for controller 110 and the memory for storing stimulus pattern data and to control various components of system 100 while a separate computing device is used to record and process signals received from sensor 106. In some embodiments, a FPGA is used for precise control and sequencing of individual mirror elements illumination properties of multiple sources, and for providing synchronous triggers to a measurement system.

In embodiments that utilize a LED, the LED typically has a Gaussian shaped spectrum with a spectral width of about 5% of the peak wavelength. In some embodiments used for cone investigations, light source 105 comprises a LED that emits somewhere within the spectral region of for example, but not limited to, 520 nm to 590 nm where the photopic response of the eye is greatest. In some embodiments used for rod investigations, light source 105 comprises a LED that emits in the shorter blue wavelength region, for example, but not limited to, between 450 nm and 510 nm. In some embodiments, the use of blue light allows for the B cones of the retina to be isolated. In addition, the use of blue light can be advantageous in certain circumstances as blue light is coupled with many bipolar cells. Other embodiments, which may be used for other types of investigations, utilize a light source 105 that comprises white light LEDs. In addition, in some embodiments, white light is used for bleaching parts of the retina. Still other embodiments may utilize a light source 105 that provides illumination anywhere in the visible spectrum.

In various embodiments, the LED has sufficient radiance to be able to launch into the eye sufficient energy in the exposure period while the illuminating beam is shaped by optics 115 such that the eye is illuminated over a viewing angle of typically 40 degrees and passing through a small area, e.g., of diameter 1 mm, located in the eye lens. In various embodiments, energy levels on the order of tens of microjoules would be appropriate. Some embodiments utilize suitable LEDs that are commercially available having emission areas of about 1 mm square and having a conversion response of 0.2 Watts/ampere. Such LEDs emit in an approximately Lambertian spatial profile and should be used with a powerful condenser lens. Some LEDs are made with an integral immersion lens that improves the efficiency.

In various embodiments, system 100 addresses many of the shortcomings of the prior art.

For example, in some embodiments of ERG system 100, the light spectrum of light source 102 is optimized for stimulation of the retina. This is in contrast to the light emitted by some previous systems, such as those that utilized CRT or LCD displays as light sources, and therefore the light spectrum of those systems was optimized for display purposes and not excitation of the retina.

In various embodiments of system 100, the light pulse energy is accurately known and is independent of pupil size. In addition, in some embodiments, system 100 comprises an ophthalmoscope where the eye is closely engaged with the illumination lens housing and therefore shielded from environmental light, thus rendering the method relatively insensitive to perturbation from the ambient light level and avoiding the need for a dim room.

This is in contrast to the light emitted by some previous systems, such as those that utilized CRT or LCD displays as light sources and did not account for variations in response of pupils of individual patients. In other words, known systems did not account for such factors as different people having different pupil sizes in the same light conditions. Accordingly, in known systems, the light energy reaching the pupil was not known and varied from patient to patient.

In various embodiments of system 100, the light pulse energy is sufficient to generate a high quality image. In particular, in various embodiments, the light energy that reaches the pupil can be accurately controlled as described herein. In addition, in various embodiments, system 100 is capable of illuminating the retina with very high power, limited only by the needs of patient comfort and safety.

In contrast, in known systems, the light that reached the retinal could not be accurately controlled and therefore the light energy reaching the retina may not always be sufficient to generate a high quality image.

In various embodiments of system 100, the dynamic response of the illumination arrangement is fast and well controlled. In particular, in various embodiments, a very high potential frame rate can be used. In some embodiments, the change between frames typically occurs at about one microsecond.

In addition, in some embodiments of assessment system, all the illumination pixels can be controlled simultaneously, enabling a global shutter effect rather than a rolling shutter effect.

Moreover, in various embodiments of system 100, during the switchover process, the light sources can be fully extinguished, so preventing any light from momentarily illuminating other parts of the retina.

In contrast, in known systems, the light sources used, such as CRT and LCD displays, had response times that were less than desirable for ERG applications and they could not be controlled as well as light source 105.

In general the above described features of various embodiments of system 100 should be compared to known systems that use Cathode Ray Tubes (CRTs) or LCD screens. These are relatively slow, generate a low level stimulus, are susceptible to ambient light interference, present a rolling shutter form of image, are generally incapable of providing a wide spectral range, and do not switch between frames without producing unwanted light. Overall, the prior art methods come with image artifacts all of which degrade the quality of the ERG/VEP measurement.

Another example of known system uses DLPs or LCDs in the projection mode and is adapted directly from commercial video projectors. While these devices are capable of creating good quality images for the purposes of viewing, they introduce a host of invisible artifacts that degrade their utility for ERF/VEP. The requirement for using a projection spatial light modulator is having a custom driver/controller with full temporal control of every pixel.

As mentioned above, some embodiments of system 100 also include eye monitor 140, infrared source 145 and beam combiner 150. In some embodiments, eye monitor 140 comprises an ophthalmoscope. Some embodiments of system 100 allow for further improvement over known systems by using properties usually associated with the ophthalmoscope. In particular, in some embodiments of system 100, the retina is simultaneously illuminated in the infrared region of the spectrum though the use of infrared source 145 and its image is observed using eye monitor 140, which in some embodiments is an ophthalmoscope.

In various embodiments, the image projected upon the retina can be directly viewed through the ophthalmoscope and thereby adjusted to be in good focus. Moreover, in some embodiments, the retina can also be almost simultaneously illuminated with infrared light that can be used to observe the vasculature and assess perfusion, both responding to the visible stimulation. In some such embodiments, the infrared light may be temporally interleaved with the visible light.

In various embodiments, the infrared illumination path of infrared source 145 is combined with the illumination path of light source 105 using a suitable beam combiner 120. In some embodiments, beam combiner 120 could be, for example, a nominally 50/50 beamsplitter, or one that uses a different ratio such as 70/30, or one that has dichroic properties to enhance the transmission at one wavelength, e.g., in the visible region, while enhancing the reflection at a different wavelength, e.g., in the infrared region. The ophthalmoscope image will show both the retinal blood vessels disposition and the DMD projection pattern, enabling the pattern to be accurately registered to the retina. This addresses another shortcoming of previously known systems where the retinal location of the coded pattern was not accurately known.

In addition, in various embodiments of system 100 that include eye monitor 140, eye monitor 140 is used to monitor the stability of eye 120 so that data collection can be suspended or discarded if the eye visual axis moves, which may occur for example if patient 125 looks away from fixation target 135. In various embodiments, eye monitor 140 comprises an ophthalmoscope. In other embodiments, eye monitor 140 is an eye tracker that operates with separate off-axis infrared illumination. In some such embodiments, infrared source 145 is used to project infrared light through DMD 110 but not through beam combiner 150. Accordingly, in some such embodiments, the infrared light is not used for flood filling on a separate beam splitter path.

In various embodiments, the systems and methods described herein provide for extremely comprehensive and precise grooming and control of the illumination forming an image on the retina.

For example, various embodiments of system 100 enable any combination of different spectral sources, including relatively narrowband LEDs or broadband white (phosphor based) LEDs, and infrared LED or laser sources.

In addition, some embodiments of system 100 enable any individual or collective setting of intensity (brightness) by using either or both control of the LED or semiconductor laser source drive current amplitude and pulse duty cycle such as the use of pulse width modulation.

In addition, some embodiments of system 100 enable any temporal arrangements applying to the sources either collectively or individually. Thus the duration of successive frames may be varied and different temporal patterns can be applied to different sources. These patterns are typically of the pulsed (on/off) type and the switching time is very fast, typically one microsecond. Moreover, the temporal changes across the illumination pattern are not dependent on the source device or the spatial location within the pattern. They can be fully synchronized to operate simultaneously or separated with preset delays.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Some aspects of embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The controller 110 is the center of the system and controls all critical timing with great accuracy, manages the illumination and emits all necessary triggers to record subject responses.

The DMD has a memory where the next desired state of each of the mirrors is loaded by parallel memory updates from the controller 110. Then a global reset switches the state of all the mirrors to the new state at the same time. This change of all the mirrors is accomplished in about 1 microsecond. This makes the DMD device ideal as a optical stimulator since there is no latency between pixels or row updates and the entire stimulus field changes at the same time. In the DMD chosen for the first implementation the full memory could be loaded in 140 microseconds. With some settling time before and after the global switch this means that a maximum frame rate of ~6800 frames per second is achievable.

The stimulus controller is programmed by the master computer over a dedicated path and various programs can be loaded. There is also an additional independent path to load a command stream into the stimulus controller from the master computer. The stimulus controller can then execute a number of different functions depending on hardware triggers or switches or on commands delivered over the data interface.

The new controller can handle a number of image types:
bitmap images, i.e. where one bit is sent to represent the desired state of each mirror. A number of such bitmaps may be uploaded to the FPGA and then displayed by a frame instruction. Bitmap images may additionally be compressed to achieve higher frame rates.
internally generated graphic images, where the FPGA generates a stream of images according to a program loaded into it from the master computer
vector graphics images, where geometrical primitives such as shapes, lines and polygons are sent to the FPGA and interpreted and displayed as pixel data
images derived from an 'object map'. In this case an object map is preloaded to the FPGA and then a series of frame instructions is sent to generate the display. The object map consists of a byte (or two) per pixel, indicating which pattern or patterns the pixel belongs to. Then for each frame a single bit for each possible object indicates whether to show it for the frame or not. This method allows for an extremely compact data stream to drive the stimulus controller and can generate a continuous display of graphic images at a very high frame rate for a modest data rate on the command interface.

Illumination

Having the illumination separate from the image generation affords many advantages. The DMD will transmit (through the cover glass) and reflect (from the mirrors) light from 360 nm to over 1000 nm with at least 50% efficiency. This allows a very large range of wavelengths to be used as stimuli or as observing wavelengths (in an ophthalmoscope). Given full control over illumination by the stimulus controller, light sources such as LEDs can be driven by variable currents, for different PWM (Pulse Width Modulation) cycles, or for short bright impulses. Given the efficiency of the Maxwellian projection system, very bright stimuli can be created, the equivalent of tens of thousands of candelas/sq.m on a viewed display at a meter distance from the patient.

Various embodiments disclosed herein address a variety of the limitations of the prior art. In contrast to some known systems, various embodiments described herein project stimulus images directly upon the retina instead of upon an intermediate screen for viewing by the patient. In some embodiments, the projection arrangement may be associated with an eye monitor that can continuously monitor the patient fixation point and be used either to move the image, maintaining the fixation target at the patient fixation point or to identify and discard stimulus image data captured during periods when the patient fixation point wanders from the target.

The aggregation of two optical systems, one to project light on to the retina and the other to capture images of the retina is fundamental to the operation of an ophthalmoscope. Based on the present disclosure, a person skilled in the art may appreciate that such a design lends itself to be adapted for the projection of images on to the retina in addition to the collection of retinal images and the incorporation of an eye tracker that uses an anterior reflection.

Projection on the retina normally employs a Maxwellian illumination arrangement where each ray associated with a point on the projected image passes close to the centre of the eye lens and is associated with an angle with respect to the optical axis joining the centre of the eye lens and the centre of the fovea. The overall projected beam pencil converges to a minimum area as it passes through the lens and is slightly larger as it passes through the adjacent iris. The total beam is captured by the retina, independent of the pupil size. This enables the total power projected to be accurately known and also enables a high power to be used, subject to patient safety and comfort.

Various embodiments disclosed herein make use of a display that employs micro-electromechanical systems (MEMS) technology. In some such embodiments, an array of very small mirrors is controlled such that each mirror can deflect light in either of two directions, typically by plus or minus 24 degrees. (There is a third position where no voltage is applied and the deflection is zero.) The array is placed in the image plane of the projector such that one direction corresponds to a contribution to the projected image while the other direction does not. The array device is called a digital micro-mirror device (DMD) and is commonly used within a digital light projector (DLP). DLP's are used in theatres and miniature versions are being applied to devices such as cell-phones and tablet computers.

The DMD is normally used as a binary spatial light modulator (SLM) that operates almost independently of the spectrum of the source light. Accordingly, various embodiments described herein can utilize a wide range of optical sources that can be optimized for ERG purposes. For example, in various embodiments, the DMD can be used with almost any wavelength or wavelength combination, with lasers, with light-emitting diodes (LEDs), or incandescent sources, in the visible, infrared and ultraviolet spectral regions.

The ability of the DMD to switch in less than a microsecond permits the ERG response to be limited by physiological phenomena rather than determined by or influenced by the optical source.

It will be appreciated from the foregoing description that optical stimulators according to the various embodiments of the invention would allow for one or more of the following features:

A variable display time, i.e. no fixed frame rate, which is just an artifact from the computer display and video world.

Have a synchronous pixel update, i.e. all pixels change to the next frame at the same time Be directly controllable, i.e. completely deterministic in timing Allow great flexibility in selecting spectral content of the stimuli. This would ideally allow for stimuli from the UV (rats have cones with a peak sensitivity at 360 nm) all the way to the NIR (to allow for non-perturbing setup of measurements on humans and animals Be capable of very fast changes of the displayed stimuli. This would allow a number of stimuli to be displayed each of which would have its own characteristic flicker frequency Allow for use of true impulse stimuli, as short as microseconds Allow for a wide range of luminance (ideally up to tens of thousands of candelas/sq. meter)

Allow for more repeatable and deterministic illuminances of the stimuli on the retina.

Be capable of integration into ophthalmoscopes to allow for accurate targeting by observing (and possibly recording) the images of the stimuli on the retina.

Allow effective targeting of stimuli on anesthetized animals

Be sufficiently responsive to allow for dynamic targeting of stimuli on fixed locations on the retina at modern camera speeds i.e. at greater than 500 frames per second.

Allow either polarized or unpolarised light to be used.

The scope of the present invention is not limited to the specific embodiments described hereinbefore but may embrace various combinations of the features listed below:

In some embodiments, the sensor is an electroretinogram (ERG) sensor.

In some embodiments, the sensor is Visually Evoked Potential (VEP) sensor.

In some embodiments, the optics project the image pattern onto the eye such that the retinal image energy of the coded image pattern projected onto the retina of the eye is independent of a pupil size of the patient.

In some embodiments, the system further comprises a fixation target for providing a target for the patient to gaze at.

In some embodiments, the first light source comprises a light emitting diode (LED). In various embodiments, the LED emits light in a spectral region substantially between 520 nm and 590 nm.

In some embodiments, the processor is coupled to the light source and wherein the processor is further configured to control the light source.

In some embodiments, the system further comprises a storage medium. In various embodiments, the processor is configured to store the processed electrical signals on the storage medium.

In some embodiments, the processor is further configured to determine a retinal response field based on the processed electrical signals.

In some embodiments, the processor is further configured to determine a matrix of retinal response values based on the processed electrical signals.

In some embodiments, the system further comprises a display and the at least one processor is configured to display the matrix on the display.

In some embodiments, the system further comprises an eye monitor for monitoring a stability of the eye.

In some embodiments, the at least one processor is further configured to discard signals produced by the sensor based on the stability of the eye.

In some embodiments, the eye monitor comprises an ophthalmoscope.

In some embodiments, the eye monitor comprises an eye tracker.

In some embodiments, the system further comprises an infrared source. In some embodiments, the illumination path of the infrared source is combined with an illumination path of the light source.

In some embodiments, the system further comprises a beam combiner. In some embodiments, the beam combiner comprises a beam splitter.

In a further embodiment, there is provided a method of measuring the response of a retina of a patient to light, the method comprising: projecting an image onto the retina; and measuring the response of the retina.

In some embodiments, a retinal image energy of the image projected onto the retina of the eye is independent of a pupil size of the patient.

In some embodiments, measuring the response of the retina comprises measuring a response of an optical nerve and determining the response of the retina based on the response of the optical nerve.

In some embodiments, measuring the response of the retina comprises sensing the Visually Evoked Potential (VEP), which is the electrical response transported through the optical nerve. In some embodiments, this is achieved using a VEP sensor.

In some embodiments, the image is projected using light in the spectral region 520 nm to 590 nm.

In some embodiments, the image is projected using a light emitting diode.

In some embodiments, the method further comprises generating a coded image pattern for projecting onto the retina.

In some embodiments, the method further comprises generating a plurality of coded image patterns for sequentially projecting images onto the retina.

In some embodiments, the method further comprises measuring the response of the retina to the sequential images.

In some embodiments, the method further comprises recording the response of the retina to each of the sequential images.

In some embodiments, the method further comprises reconstructing a retinal response field based on the response of the retina to the sequential images.

In some embodiments, the method further comprises generating a matrix of retinal response values.

In some embodiments, the method further comprises displaying the matrix of retinal response values.

In some embodiments, the method further comprises monitoring a stability of the eye.

In some embodiments, the method further comprises disregarding the response of the retina based on the stability of the eye.

INDUSTRIAL APPLICABILITY

Optical stimulators according to various embodiments of this invention can be used for the standard mfERG, focal ERG, PERG and VEP experiments but also open the way for new stimulus patterns which take advantage of the very high frame rates, fast and global frame switching, spectral selectivity and high luminance levels now available. The flexible drivers available now allow the easy design of custom patterns that can be mapped out for each patient by fitting patterns to potential scotomas. We have designed and built software that runs on the master computer that allows a user to design custom stimuli in an interactive fashion. A digital image of the subject's retina can be displayed and the user can create, move, resize, group and move as a group the stimuli over the retinal image. The object map representing these patterns can be uploaded over the data interface to the stimulus controller and then a diagnostic test run. One particular capability that comes from the very high frame rate is that each of many objects can be given their own flicker speed. That is, each object can have its own characteristic rate for switching on and off but all the stimuli are active at the same time and the ERG equipment is collecting the sum of all the responses. Since the DMD can change frames every 150 microseconds, each object can have its own flicker rate with a jitter of only +/−75 microseconds. This kind of experiment is not possible on CRTs or LCDs, however custom LED arrays have been built to exploit this flicker measurement [Linderberg]. The data can be extracted using either a simple Fourier transform or by a method known as cyclic summation. Tests on embodiments herein have been carried out using four stimuli flickered at 9, 10, 11, and 12 Hz with satisfactory results.

The new capabilities of the optical stimulator allow for extensions to be made to common diagnostic methods such as microperimetry. One such is the availability of much brighter stimuli than a LCD screen can produce (LCDs are commonly used for this application). This can be important when examining patients with poor vision. A second is dynamic tracking microperimetry which uses the new optical stimulator and an imaging ophthalmoscope with a fast digital camera. The fast camera can generate a stream of retinal or choroidal images which can be used to generate registration information. This registration information can be used to reposition the microperimetry target on the desired location so that microperimetry measurements can be carried out on subjects with poor or no fixation capability. The latter case is very important, in that early clinical trials with experimental drugs for treating retinal conditions are usually carried out on patients with very little remaining vision. The optical stimulator is so fast in repositioning (~150 microsceconds) that the fast camera and processing the images to generate registration information is the rate limiting step. However fast, sensitive cameras with full resolution frame rates of over 100 frames/sec are becoming common and just using a portion of the image (region of interest) can boost the rate to close to 1000 frames/sec and still yield registration information.

With the fast update of the new optical stimulator targets can be moved very smoothly at various speeds across the patient's visual field. This opens up new possibilities for exploring the detection of fast transients in the parafoveal and foveal areas.

A further use of the new optical stimulator involves presenting text to the subject via the optical stimulator mounted in an imaging ophthalmoscope with a fast camera. This actually allows the user to see where exactly where the preferred location is on the retina where the subject is reading the text. This capability may allow the development of customized text sizes and layout to be developed for each patient. This is of great significance given the growing prevalence of AMD (Age-related Macular Degeneration) which destroys some areas of the retina while typically sparing others.

Although embodiments of the invention have been described and illustrated in detail, it is to be clearly understood that the same is by way of illustration and example only and not to be taken by way of limitation, the scope of the present invention being limited only by the appended claims.

CITATIONS

Non-Patent Literature

Packer: O. Packer et al.: Vision Research 41 (2001) 427-439
Kuchenbecker: Journal of Vision Dec. 31, 2009 vol. 9 no. 14 article 43
Lindenberg: Graefes Arch Clin Exp Ophthalmol. 2003 June; 241(6):505-10.

The invention claimed is:

1. A system for measuring response of a retina of an eye of a subject to light, comprising:
    at least one digital micro-mirror device (DMD) having micro-mirrors;
    a controller for controlling the DMD to configure the micro-mirrors to form a stimulus pattern;
    a light input for directing light to the DMD;
    optics positioned and configured to receive light reflected from the patterned micro-mirrors and direct the reflected light to the eye of the subject to image the stimulus pattern onto the retina as a stimulus image;
    a sensor unit for providing an output signal indicative of a response evoked by the retina to the stimulus image; and
    at least one processor for processing the output signal in relation to the stimulus pattern to enable an assessment of the functionality of the retina.

2. The system according to claim 1, wherein the controller comprises data storage for storing sets of data, each set of data for formation of a respective one of a plurality of said stimulus patterns, each set associated with a respective pattern identifier, and an interface for receiving identifiers selectively to select the stimulus patterns for application to said DMD device.

3. The system according to claim 2, wherein said data storage stores a predetermined number of sets of pattern data and the controller is configured to cause the data storage to discard sets of data for patterns already applied to the DMD, to provide capacity for newly received sets of pattern data.

4. The system according to claim 3, wherein the controller is operable to accumulate in said data storage sets of data for a predetermined number of stimulus patterns and apply the accumulated stored patterns to the DMD device substantially simultaneously when said predefined number have been accumulated.

5. The system according to claim 4, wherein the controller is operable to output a trigger signal substantially concurrently with applying said predefined number of stored patterns to the DMD, said trigger signal serving for synchronization of one or more external devices.

6. The system according to claim 1 wherein the controller is configured to output a control signal for control of the light input.

7. The system according to claim 1 further comprising a computing device for communicating with said controller and transmitting said pattern data for storage and said identifiers for subsequent selection thereof.

8. The system according to claim 1 wherein the eye of the subject has a pupil further comprising optics for capturing light passing from the retina to emerge through the pupil and combining the captured light with the stimulus pattern image to display a fundus image of the retina and stimulus image superimposed.

9. The system according to claim 8, further comprising an illumination device for lighting the retina from behind, the fundus image comprising light reflected from and light transmitted through the retina.

10. The system according to claim 1, wherein the sensor is an electroretinogram (ERG) sensor or a Visually Evoked Potential (VEP) sensor.

11. The system according to claim 1, wherein the light input is an LED which emits light in a spectral region substantially lying within the spectral region corresponding to the human visual response.

12. The system according to claim 1, wherein the light input comprises a beam combiner for combining an illumination path of an infrared source with an illumination path of a second light source.

13. A method of assessing functionality of a retina of an eye of a subject to light, comprising:
    using a controller to configure micro-mirrors of a digital micro-mirror device (DMD) to form a stimulus pattern;
    directing light to the DMD;
    using optics to receive light reflected from the patterned micro-mirrors and direct the reflected light to the eye of the subject to image the stimulus pattern onto the retina as a stimulus image; and
    using a sensor unit to provide an output signal indicative of a response of the retina of the subject evoked by the stimulus image.

14. The method according to claim 13, further comprising storing sets of data in a storage unit of the controller, each set of data for generation of a respective one of a plurality of said stimulus patterns, each set associated with a respective pattern identifier, and supplying identifiers selectively to the controller to select the stimulus patterns for application to said DMD device.

15. The method according to claim 13 wherein the eye of the subject has a pupil, further comprising capturing light passing from the retina to emerge through the pupil and combining the captured light with the stimulus pattern image to display a fundus image of the retina with the stimulus image superimposed.

16. The method according to claim 15, further comprising applying light behind the retina, the fundus image formed by light reflected from and light transmitted through the retina.

17. The method of claim 16, wherein measuring the response of the retina comprises measuring optical nerve response and determining the response of the retina based on the response of the optical nerve.

18. The method of claim 17, wherein measuring the response of the retina comprises sensing a Visually Evoked Potential (VEP) or an electrical nerve impulse using ERG.

19. The method according to claim 13, further comprising using a beam combiner for combining an illumination path of an infrared source with an illumination path of a second light source.

20. An optical stimulator for providing light for optical stimulation of a retina of an eye of a subject, comprising:
   a micro-mirror device (DMD) comprising an array of micro-mirrors;
   a controller for controlling the DMD to configure the micro-mirrors to form a stimulus pattern, said controller having a data storage for storing sets of data, each set of data for generation of a respective one of a plurality of said patterns, each set associated with a respective pattern identifier, and an interface for receiving identifiers selectively to select the patterns for application to said DMD device; and
   a light input for directing light to the DMD;
   the optical stimulator configured such that light reflected from the patterned micro-mirrors can be directed by juxtaposed projection optics to the eye to form an image of the corresponding stimulus pattern onto the retina of the eye of the subject.

* * * * *